(12) United States Patent
Shin et al.

(10) Patent No.: US 7,141,424 B2
(45) Date of Patent: Nov. 28, 2006

(54) SOLELY POLLEN-SPECIFIC PROMOTER

(75) Inventors: Jeong Sheop Shin, Seoul (KR); Beung Tae Ryu, Seoul (KR); Sung Chul Bahn, Seoul (KR); Hae Jin Kim, Seoul (KR)

(73) Assignee: Korea University Industry& Academy Cooperation Foundation, Seoul (KR)

( * ) Notice: Subject to any disclaimer, the term of this patent is extended or adjusted under 35 U.S.C. 154(b) by 139 days.

(21) Appl. No.: 10/977,882

(22) Filed: Oct. 29, 2004

(65) Prior Publication Data

US 2005/0132447 A1   Jun. 16, 2005

(30) Foreign Application Priority Data

Oct. 29, 2003   (KR) ..................... 10-2003-0076000

(51) Int. Cl.
C12N 15/82   (2006.01)
C12N 5/14   (2006.01)
A01H 1/00   (2006.01)

(52) U.S. Cl. ................. 435/419; 435/320.1; 536/24.1
(58) Field of Classification Search ............... 536/24.1, 536/23.1; 800/287; 435/320.1
See application file for complete search history.

(56) References Cited

U.S. PATENT DOCUMENTS

| 6,372,967 B1 * | 4/2002 | Mariani et al. ............. 800/303 |
| 6,476,297 B1 | 11/2002 | Mascarehas et al. ........ 800/303 |
| 6,740,748 B1 | 5/2004 | Knox et al. ................. 536/23.6 |
| 2003/0061635 A1 | 3/2003 | Reddy et al. ............... 800/287 |

FOREIGN PATENT DOCUMENTS

| EP | 1081223 | 7/2001 |
| JP | 2000300273 | 10/2000 |
| WO | WO 96/17945 | 6/1996 |
| WO | WO 99/42587 | 8/1999 |

OTHER PUBLICATIONS

Kim Y, Buckley K, Costa MA, and An G. (1994) A 20 nucleotide upstream element is essential for the nopaline synthase (nos) promoter activity. Plant Molecular Biology, vol. 24, pp. 105-117.*
Mitsuda N, Takeyasu K, and Sato MH. (2001) Pollen-specific regulation of vacuolar H+-PPase expression by multiple cis-acting elements. Plant Molecular Biology, vol. 46, pp. 185-192.*
Bray-Allen S, Quail M, Harris B, Rajandream MA, and Barrell BG. (1999) GenBank Accession AL096692.1.*
Hyun Uk Kim; *Production of Male Sterile Tobacco Plants Using an Anther-Specific Promoter Recombinant* (Aug. 1995), 135 pages [with English abstract—3 pages], Dept. of Natural Fiber, Seoul National University.
E. Zabaleta, V. Heiser, L. Grohmann and A. Brennicke; Promoters of nuclear-encoded respiratory chain Complex I genes from *Arabidopsis thaliana* contain a region essential for anther/pollen-specific expression (1998), pp. 49-59, *The Plant Journal* 15(1).
DATABASE EMBL 'Online!; Mar. 16, 2000, "*Arabidopsis thaliana* DNA chromosome 4, contig fragment No. 71"; XP002312137 retrieved from EBI accession No. EM_PRO:AL161575; Database accession No. AL161575; Positions 20370-20920.
Iris Ottenschlager, Ioulia Barinova, Victor Voronin, Marlis Dahl, Erwin Heberle-Bors & Alisher Touraev, Green flourescent protein (GFP) as a marker during pollen development (1999), *Transgenic Research* 8:279-294.
Sung Chul Bahn, Hyoung Yool Lee, Hae Jin Kim, Stephen B. Ryu, Jeong Sheop Shin, Characterization of Arabidopsis secretory phospholipase $A_2$~Y cDNA and its enzymatic properties[1] (2003), FEBS Letters 553 (2003) 113-118.
Hyoung Yool Lee, Sung Chul Bahn, Yoon-Mi Kang, Kyu Hee Lee, Hae Jin Kim, Eun Kyeung Noh, Jiwan P. Palta, Jeong Sheop Shin, and Stephen B. Ryu, Secretory Low Molecular Weight Phospholipase $A_2$ Plays Important Roles in Cell Elongation and Shoot Gravitropism in *Arabidopsis* (Sep. 2003), *The Plant Cell*, vol. 15, 1990-2002, American Society of Plant Biologists.
Sung Han Ok, Hyun Mi Park, Ji Young Kim, Sung Chul Bahn, Jung Myung Bae, Mi Chung Suh, Ji-Ung Jeung, Kyung-Nam Kim, Jeong Sheop Shin, Identification of differentially expressed genes during flower development in carnation (*Dianthus caryophyllus*) (2003), *Plant Science* 165, pp. 291-297.
Katsunori Hatakeyama, Sumie Ishiguro, Kiyotaka Okada, Takeshi Takasaki and Kokichi Hinata, Antisense inhibition of a nuclear gene, BrDAD1 in *Brassica* causes male sterility that is restorable with jasmonic acid treatment (2003), *Molecular Breeding* 11:325-336.

* cited by examiner

Primary Examiner—Ashwin D. Mehta
Assistant Examiner—Cathy Kingdon Worley
(74) *Attorney, Agent, or Firm*—St. Onge Steward Johnston & Reens LLC

(57) ABSTRACT

An isolated solely pollen-specific promoter derived from *Arabidopsis* comprise a nucleotide sequence of *Arabidopsis* $PLA_2$-δ gene. The novel promoter has specific roles in particular organs and at particular developmental stages, such as in mature flowers, and can be used in the production of hybrid seeds using male sterility techniques.

6 Claims, 5 Drawing Sheets

Fig. 2

```
AGGAGAGTAACAATAACTTGAAGATTGTGTAATCCCCTCCGTTTTAGTTTTCATGATTC
TCTCTTGAATCAATTTTTTCCAGTTTATCCCTGAAACGGAGGCTTTGAAGCTTGAGAAA
AATCCATTTTGCTATAACTCTTTGATAAAGGTTGCTCTCAATAAGAACAAAATTTCCCAG
GAAATTGCTTTCACTATAATGTTTTTGTCCTTGTTAATATCAATATCAGCAATGATACA
AAATTTGAAACCATATATTATCATTTGCAATCTAATAAATATCGTTTCTAAAGATTATGTA
GATCTTCATGATACTCTGTTCTTAACATCCATAATTTTATTTTTGATAAAGAACGGCC
ATAAAATTTGGTGGTTGATTGGTAATCATGAAGACCAAGAATCATATATGAGAAAG
AGGAGGGACGAGAAAGCAGGAGGACCAAGAATTTGAAAGAACAAACAACAAACACAAT
TATAATTCTTGGGGTCAGAATTTGAAAGAACAAACAACAAACTTCTACTGGAGAAGGTA
AGATAGAAAC
```

* AGAAAA : Pollen specific element

* LB : left border
* RB : right border

Fig. 4

AAGCTTAACTTGAAGATTGTGTAATCCCCTCGGTTTTAGTTTTCATGATCTCTCTCTTGAATCAATTTTTTTTCCAGTTTATCCCTGAAACGGAGGGCTTTGAAGCTGAAG
*HindIII*
AAAAATCCATTTTGCTATAACTCTTTGATAAAGGTTGCTCTCAATAAGAACAAAATTTCCCAGGAAAATTGCTTCACTATAATGTTTTTGTCCTTGTTTAATATCAATA
TCAGCAATGATACAAAATTTGAAACCATTATATCATTTGCAATCAATAAATATCGTTTCTAAAGATTATGTAGATCTTCATGATACTCTGTTCTTAACATCCATAAT
TTTATTTTTGATAAAGAAGAACGGCCATAAAAATTTGGTGGTTGATGGTAATCGTAAACGTCTTCTTTTTTTTTACATATGAGAAAGAGGAGGACGAGAAAGCAGGAGGA
CCAAGAATGGGACCTCCATTCCAAAGACACAATTATAATTCTTGGGGTCAGAATTGAAAGAACAAAACAACAAACTTCTACTGGAGAAGGTAAGATAGAAACATG
GGATCCCCGGGTGGTCAGTCCCTTatgttacgtcctgtagaaaccccaaccegtgaaatcaaaaaactcgacggcctgtggcattcagtctggatcgcgaaaactgtg
*BamHI*
Gaattgatcagcgttgtggaaagccggcgttacaagaaaccggcaattgctgtgccaggcagttttaacgatcagttcgccgatgcagatattcgcgatgcggg
caacgtctctggtcagcgcgaagtctcttttatacggaagttgggcaggcagcgtatcgtgctgctttcgatgcgttcactcattaccgccaagtgtggtcaatat
caggaagtgatggagcatcaggggctatcaggcccattgaagccgtatgttattgccgggaaagtgtacgtatcaccgttgtgtgaacaacgaac
tgaactggcagactatccgccggaatggtgattaccgacgaaaagccaagaaaaacagtcttacttcctcatgattcttaactatgccgaatccatcgcagcgt
aatgcttctacaccgcgaacactggtgacgatatcaccgtttgtgcaactgcggcagttgcctgacactagcgcgtcgccaagacgtgtaacacacgggtcaatggt
gatgtcagccgttaactgcgtgatgcgtgtcaactgacggtgcaactagcacccggttgatcggcactgagccgtgaatcggcaaccactctcctgat
gttatctctatgaactgtcgtcacagccagaaagccagacagagtgtgatatctaccgcttcgcgtgcatcgcgtcaggcgcagtgaaggcaacagttcctgat
taaccacaaaccgttctacttttgtcgtcatgaagatgcgggactttagctgcaaaggattcgataacgtgctgatggtcacgaccacgcattaatggac
tggattgggccaactcctaccgtacctgccattaccctcgaagaagatgctcgactggcagatgaacatggcatcgttggtgattgaatgcctgctacgagcgat
gctttaacctctctcttaggcattgttcgaagcgggcaacaagcgaagttgatgtgagtagttgccaactcaagtcaacaaccgtccgcaagtcacggaatatttcgcactgcg
taaagagctgatagcgcgtgacaaaaaccaccaagcgtggtggtgcaactgccgatcacctgccgtcatgtaatgttctgcgacgctcacaccagcgatctcttgatgtcgtgctga
gaagcaacgctaaactgaccgacgcgtccgatcacctcgcaagcggcgatttggaaaacgcagagaagtactgcaggaaaagaactctgcggtgcatcagccgattatcat
accgttattacggatgtatgtccaagcggcgttagccggctagcacttcgcactcaatgtaccgacatgtggagtgaagtatcagtgtcatggctggatgtatcaccgcgtcttgat
caccgaatacgcgtggatacgttagccggtatgctgcaacaggtatgaatttgcgacctcgcaagcatattgcgcgttgccgttaacaagaaaggatcttcactcgcgacc
cgcgtcagccagccgtcgtcggtgaacaggttatgaatttgcgaactgactcggtgaaacgcgaggaggcaacaatgaATCAACAACTCTCGTGGCGC
gcaaaccgaagtcggccgccttcttctgctgcaaaaacgctggactgactcggtgaatgaacgcgaggaggcaacaatgaATCAACAACTCTCGTGGCGC
ACCATCGGTCGGCTACAGCCTCGGGAATTCGACCGAGGCTGGAAATTCCCGATCGTTCAAACATTTGGCAATAAAGTTCTTAAGATGATTAAGATGGGTTTTATGATTAGAGATGGGTTTTTATGATTAGAGTCCCGCAATTA

*SacI*

GATGATTATCATATAATTCTGTTGAATTACGTTAAGCACATGTAATAATTAACATGTATGACGTTATTTATGAGATGCATGACGTTATTTATGATTAGAGATGGGTTTTTATGATTAGAGTCGGGAATTC
TACATTTAATACGCGATAGAAAACAAAATATAGCGCGCAAACTAGGATAAATTATCGCGCGCGGTGTCATCTATGTTACTAGATGGGAATTC

*EcoRI*

* The developmental stages of flower buds are shown above (Smyth et al., 1990)

* The arrowhead indicates the flower bud of which anther is in the initiation stage of turning yellow.

* CP : callose plug

SEQUENCE LISTING

```
<160> NUMBER OF SEQ ID NOS: 6

<210> SEQ ID NO 1
<211> LENGTH: 550
<212> TYPE: DNA
<213> ORGANISM: Arabidopsis thaliana

<400> SEQUENCE: 1
aggagagtaa caataacttg aagattgtgt aatcccctcc gttttagtt ttcatgattc      60 tctcttgaat caatttttt tccagtttat ccctgaaacg gaggctttga agctgagaaa    120
aatccatttt gctataactc tttgataaag gttgctctca ataagaacaa aatttcccag   180
gaaattgctt tcactataat gttttgtcc ttgtttaata tcaatatcag caatgataca    240
aaatttgaaa ccatattatc atttgcaatc taataaatat cgtttctaaa agattatgta   300
gatcttcatg atactctgtt cttaacatcc ataattttta ttttttgata aagaacggcc   360
ataaaatttg gtggttgatt ggtaatcatg aaacgtcttc tttttttaca tatgagaaag   420
aggagggacg agaaagcagg aggaccaaga atgggacctt ccattccaaa gagacacaat   480
tataattctt ggggtcagaa tttgaaagaa caaaacaaca aacttctact ggagaaggta   540
agatagaaac                                                         550

<210> SEQ ID NO 2
<211> LENGTH: 33
<212> TYPE: DNA
<213> ORGANISM: Artificial Sequence
<220> FEATURE:
<223> OTHER INFORMATION: Primer for PCR

<400> SEQUENCE: 2
ggttggattt tccaaggaat gcccttattc aac                                33

<210> SEQ ID NO 3
<211> LENGTH: 29
<212> TYPE: DNA
<213> ORGANISM: Artificial Sequence
<220> FEATURE:
<223> OTHER INFORMATION: Primer for PCR

<400> SEQUENCE: 3
tcaagaagga gaagggttca tcggaacag                                     29

<210> SEQ ID NO 4
<211> LENGTH: 35
<212> TYPE: DNA
<213> ORGANISM: Artificial Sequence
<220> FEATURE:
<223> OTHER INFORMATION: Primer for PCR

<400> SEQUENCE: 4
gagtaagctt aacttgaaga ttgtgtaatc ccctc                              35

<210> SEQ ID NO 5
<211> LENGTH: 35
<212> TYPE: DNA
<213> ORGANISM: Artificial Sequence
<220> FEATURE:
```

<223> OTHER INFORMATION: Primer for PCR

<400> SEQUENCE: 5

```
caccggatcc catgtttcta tcttaccttc tccag                              35
```

<210> SEQ ID NO 6
<211> LENGTH: 2709
<212> TYPE: DNA
<213> ORGANISM: Artificial Sequence
<220> FEATURE:
<223> OTHER INFORMATION: the gene expression cassette containing
     AtsPLA2- -promoter, GUS, and Nos-terminator

<400> SEQUENCE: 6

```
aagcttaact tgaagattgt gtaatcccct ccgtttttag ttttcatgat tctctcttga     60
atcaatttt tttccagttt atccctgaaa cggaggcttt gaagctgaga aaaatccatt    120
ttgctataac tctttgataa aggttgctct caataagaac aaaatttccc aggaaattgc   180
tttcactata atgttttttgt ccttgtttaa tatcaatatc agcaatgata caaaatttga   240
aaccatatta tcatttgcaa tctaataaat atcgtttcta aaagattatg tagatcttca   300
tgatactctg ttcttaacat ccataatttt tatttttga taaagaacgg ccataaaatt    360
tggtggttga ttggtaatca tgaaacgtct tcttttttta catatgagaa agaggaggga   420
cgagaaagca ggaggaccaa gaatgggacc ttccattcca aagagacaca attataattc   480
ttggggtcag aatttgaaag aacaaaacaa caaacttcta ctggagaagg taagatagaa   540
acatgggatc cccgggtggt cagtccctta tgttacgtcc tgtagaaacc ccaacccgtg   600
aaatcaaaaa actcgacggc ctgtgggcat tcagtctgga tcgcgaaaac tgtggaattg   660
atcagcgttg gtgggaaagc gcgttacaag aaagccgggc aattgctgtg ccaggcagtt   720
ttaacgatca gttcgccgat gcagatattc gtaattatgc gggcaacgtc tggtatcagc   780
gcgaagtctt tataccgaaa ggttgggcag gccagcgtat cgtgctgcgt ttcgatgcgg   840
tcactcatta cggcaaagtg tgggtcaata tcaggaagt gatggagcat cagggcggct    900
atacgccatt tgaagccgat gtcacgccgt atgttattgc cggaaaagt gtacgtatca    960
ccgtttgtgt gaacaacgaa ctgaactggc agactatccc gccgggaatg gtgattaccg  1020
acgaaaacgg caagaaaaag cagtcttact tccatgattt cttaactat gccggaatcc   1080
atcgcagcgt aatgctctac accacgccga acacctgggt ggacgatatc accgtggtga  1140
cgcatgtcgc gcaagactgt aaccacgcgt ctgttgactg caggtggtg gccaatggtg    1200
atgtcagcgt tgaactgcgt gatgcggatc aacaggtggt tgcaactgga caaggcacta  1260
gcgggacttt gcaagtggtg aatccgcacc tctggcaacc gggtgaaggt tatctctatg  1320
aactgtgcgt cacagccaaa agccagacag agtgtgatat ctacccgctt cgcgtcggca  1380
tccggtcagt ggcagtgaag gccaacagt cctgattaa ccacaaaccg ttctactta     1440
ctggctttgg tcgtcatgaa gatgcggact acgtggcaa aggattcgat aacgtgctga   1500
tggtgcacga ccacgcatta atggactgga ttggggccaa ctcctaccgt acctcgcatt  1560
acccttacgc tgaagagatg ctcgactggg cagatgaaca tggcatcgtg gtgattgatg  1620
aaactgctgc tgtcggcttt aacctctctt taggcattgg tttcgaagcg gcaacaagc    1680
cgaaagaact gtacagcgaa gaggcagtca acggggaaac tcagcaagcg cacttacagg   1740
cgattaaaga gctgatagcg cgtgacaaaa accaccaag cgtggtgatg tggagtattg   1800
ccaacgaacc ggatacccgt ccgcaagtgc acgggaatat ttcgccactg cggaagcaa    1860
```

```
cgcgtaaact cgacccgacg cgtccgatca cctgcgtcaa tgtaatgttc tgcgacgctc    1920
acaccgatac catcagcgat ctctttgatg tgctgtgcct gaaccgttat tacggatggt    1980
atgtccaaag cggcgatttg gaaacggcag agaaggtact ggaaaaagaa cttctggcct    2040
ggcaggagaa actgcatcag ccgattatca tcaccgaata cggcgtggat acgttagccg    2100
ggctgcactc aatgtacacc gacatgtgga gtgaagagta tcagtgtgca tggctggata    2160
tgtatcaccg cgtctttgat cgcgtcagcg ccgtcgtcgg tgaacaggta tggaatttcg    2220
ccgattttgc gacctcgcaa ggcatattgc gcgttggcgg taacaagaaa gggatcttca    2280
ctcgcgaccg caaaccgaag tcggcggctt ttctgctgca aaaacgctgg actggcatga    2340
acttcggtga aaaaccgcag cagggaggca acaatgaat caacaactct cctggcgcac     2400
catcgtcggc tacagcctcg ggaattgcta ccgagctcga atttccccga tcgttcaaac    2460
atttggcaat aaagtttctt aagattgaat cctgttgccg gtcttgcgat gattatcata    2520
taatttctgt tgaattacgt taagcatgta ataattaaca tgtaatgcat gacgttattt    2580
atgagatggg tttttatgat tagagtcccg caattataca tttaatacgc gatagaaaac    2640
aaaatatagc gcgcaaacta ggataaatta tcgcgcgcgg tgtcatctat gttactagat    2700
cgggaattc                                                           2709
```

SOLELY POLLEN-SPECIFIC PROMOTER

RELATED APPLICATION DATA

This application claims priority to Korean Patent Application No. 10-2003-0076000, filed Oct. 29, 2003.

FIELD OF THE INVENTION

The present invention relates to a solely pollen-specific promoter derived from *Arabidopsis thaliana*. More specifically, the present invention relates to the solely pollen-specific promoter which has specific roles in particular organs and at particular developmental stages, such as mature flowers, and can be used for the production of hybrid seeds using male sterility techniques.

BACKGROUND OF THE INVENTION

In many crops, hybrids ($F_1$) cross-breeded inter-species or inter-lines of species represent heterosis. These hybrids have high adaptability to environmental changes and are therefore resistant to plant diseases and environmental stresses. They can also be superior to their parents in certain desirable agricultural traits. Therefore most vegetable seeds cultivated and sold by seed companies is $F_1$ hybrids.

Because reproduction mechanisms in higher plants are very complicated, it is not easy to obtain pure hybrid seeds in large quantities without self-pollination of the parent plant taking place. In order to solve the problem and to enhance the rate of outbreeding, an artificial pollination method has been used for a long time. The artificial pollination method involves the removal of anthers or tassels from the female parent plant and artificial fertilization with pollen from the male parent plant, either manually or mechanically.

However, such an artificial pollination method is labor intensive and not altogether reliable as it is possible that some female plants may escape the detasseling process in some cases. In addition, this approach is not easily applicable to species in which the male and female floral organs are very small.

Meanwhile, in order to solve the problems of artificial pollination, another approach is also known. The approach involves the production of a male sterile line using the incompatibility allele or the male sterility gene that represses the development of pollen. For example the cytoplasm male sterile line of some crops is used for cross-breeding. However, again such a technique may cause side effects such as degradation of disease resistance and is not wholly reliable.

Another approach is to induce artificial mutation and to select male sterile lines. Chemical methods that degrade the fertility of plants are also known. However, there are some limitations in usage, since these methods lack stability and the mechanisms are not understood.

Recently molecular biological studies searching for the mechanism of male sterility, inserting the gene only inducing male sterility into the genome of a plant and breeding new plant species have been conducted. It is very effective in inducing male sterility with maintaining the desirable traits of species to use such genetic manipulation techniques. However, if the gene inducing male sterility is inserted into the genome of a plant and the expression of the gene starts from the early developmental stages of plant, it may affect adversely the growth of the plant and the desirable agricultural traits of the plant species. Therefore if a promoter region (regulating site of a gene) can regulate the expression of the gene that inhibits the growth or germination of the pollen, male sterility can be induced without affecting the development and growth of the plant.

In order to effectively produce male sterile crops having desirable agricultural traits, some researchers have studied pollen-specific promoter regions and the genetic structure comprising the promoter regions (WO 96/17945; KR Patent No. 0278819, Hyun ook Kim, Production of male sterile Tobacco Plants Using an Anter-Specific Promoter Recombinant, thesis for a doctorate, Seoul National University, 1995).

A need exists for novel promoters that have specific roles in particular organs and at particular developmental stages, such as in mature flowers to regulate male sterility.

An object of the present invention is to provide a novel pollen-specific promoter that regulates the expression of a gene only in the pollen tissue, particularly in mature pollen tissue, thereby being useful as means of production of a male sterile line.

Another object of the present invention is to provide a recombinant vector comprising the solely pollen-specific promoter, and a transformed plant cell using the promoter.

SUMMARY OF THE INVENTION

In order to accomplish the above objects, the present invention provides the solely pollen-specific promoter derived from *Arabidopsis* comprising (a) a nucleotide sequence of SEQ ID NO: 1 or (b) a nucleotide sequence substantially identical to the nucleotide sequence of SEQ ID NO: 1.

The inventors have continued the studies and located the solely pollen-specific gene (TAIR at4g29470). It was confirmed that the gene was specifically expressed only in the organ containing pollen (FIG. 1). Further, it was assumed that the promoter of the gene regulates the expression of the pollen-specific gene. Then the putative nucleotide sequence of the promoter was isolated and the nucleotide sequence was identified (FIG. 2).

Further, the expression pattern of the pollen-specific promoter fused with the reporter gene 'GUS' was studied (FIG. 5). Therefore, the novel promoter derived from *Arabidopsis* according to the present invention can induce specific expression only in pollen tissue, particularly in mature pollen tissue, thereby being useful as means of production of a male sterile line.

The expression "a nucleotide sequence substantially identical to the nucleotide sequence of SEQ ID NO: 1" with reference to the present invention means a nucleotide sequence that has any substitution of, variation of, modification of, replacement of, deletion of or addition of one or more nucleotides, but retains promoter activity inducing the pollen-specific expression of the foreign gene.

Furthermore, the present invention provides a recombinant vector comprising a promoter sequence as described the above and a foreign gene fused with the promoter and regulated by the promoter.

The foreign gene means a variable gene having a special purpose such as reporter gene confirming the expression of the promoter. In the case of producing the male sterile plant, the foreign gene may be a gene degrading the development or germination of the pollen.

An example of a gene degrading the development or germination of pollen may include a cytotoxin-associated gene such as DTx-A gene derived from *Corynebacterium diphtheriae*, this example is not meant to be construed as a limitation.

The present invention also provides a plant cell by the above recombinant vector.

Techniques known in the art of the present invention can be used to construct the recombinant vector comprising the promoter according to the present invention and to introduce the above recombinant vector into the plant cell (See, for example, Clough S J and Bent A F, 1998. Floral dip: a simplified method for *Agrobacterium*-meditated transformation of *Arabidopsis thaliana*. Plant J 16: 735–43.) For example, *Agrobacterium*-mediated transformation can be used to introduce the above recombinant vector into the plant cell.

The present invention also provides primers (SEQ NO: 4 and SEQ NO: 5) for amplifying the promoter DNA fragment comprising the sequence represented as SEQ NO: 1.

Using the pollen-specific promoter according to the present invention, the foreign gene can be expressed in targeted tissues and developmental stages, such as in a mature flower. Therefore since it is possible to regulate the time of trait expression in the cycle of development, it is also possible to prevent the problems of the foreign gene being expressed in an undesirable plant organ or tissue, or in an undesirable developmental stage.

Specifically, fusing the foreign gene degrading a pollen fertility with the pollen-specific promoter according to the present invention and introducing it into the plant cells makes it possible to express the foreign gene in mature flowers and artificially repress the development of pollen. Therefore the male sterile plant can be easily provided and used for producing $F_1$ hybrid seed.

BRIEF DESCRIPTION OF THE DRAWINGS

The invention will now be particularly described only by way of example with reference to the accompanying drawings in which:

FIG. 2 shows the total DNA sequence (SEQ ID NO: 1) of the pollen-specific promoter according to the present invention.

FIG. 4 shows the nucleotide sequence (SEQ ID NO: 6) that indicates the gene expression cassette containing AtsPLA$_2$-δ-promoter, GUS and Nos-terminator. (75 nucleotides/lane). 1. First 'ATO' is the start codon of AtsPLA2-d gene. 2. Second 'atg' is the start codon of GUS gene. 3. First 'tga' is the stop codon of GUS gene. 4. The used restriction enzyme sites were underlined. 5. The nucleotide sequence of AtsPLA2-d-promoter was indicated with a capital letter. 6. The nucleotide sequence of GUS gene was indicated with a small letter. 7. The nucleotide sequence of Nos-terminator was indicated with an italic letter.

DETAILED DESCRIPTION

Figure 1:
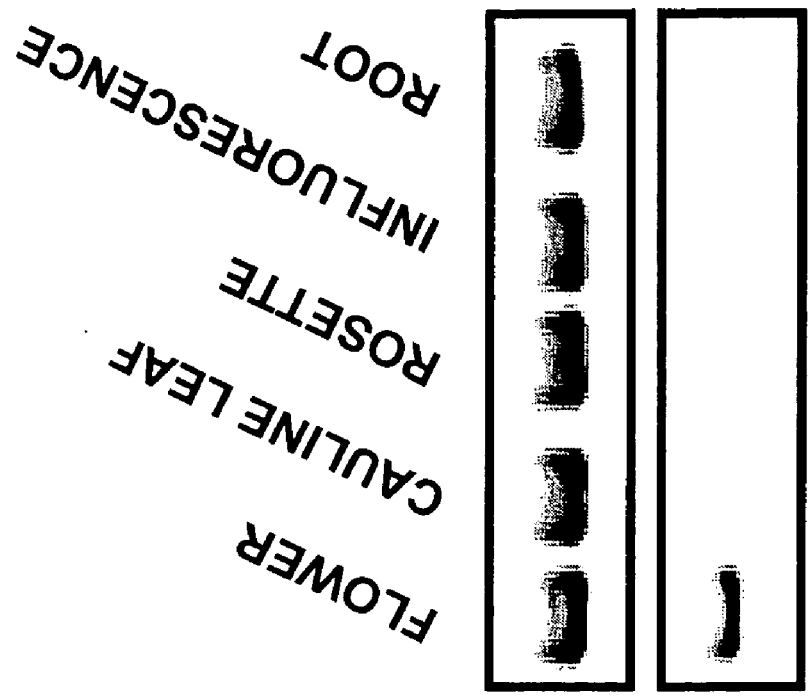
FIG. 1 shows gene transcription pattern expressed by the organ-specific promoter according to the present invention.

The following examples will enable those skilled in the art to more clearly understand how to practice the present invention. It is to be understood that, while the invention has been described in conjunction with the preferred specific embodiments thereof, that which follows is intended to illustrate, not to limit the scope of the invention. Other aspects of the invention will be apparent to those skilled in the art to which the invention pertains.

EXAMPLE 1

Discovery of Putative Phospholipase

The present inventors have cloned the putative secretory phospholipase A$_2$ (sPLA$_2$) of carnation and reported that result for the first time in a plant. The role of sPLA$_2$ in plants is not well known and that study is in the early stages. It is assumed only that it plays an important role in flower tissue, since it is abundantly found in the flower tissue.

In order to find the gene of *Arabidopsis* which is the ortholog to the putative sPLA2 found in the carnation, the inventors compared and searched the sequence database of *Arabidopsis* disclosed in the site of TAIR (The *Arabidopsis* Information Resource). Such searches for sPLA2 homologs based on the previously published carnation sPLA2 cDNA sequence enabled the identification of sPLA2-δ (At4g29470) in *Arabidopsis thaliana* 'Col-0' genome. At4g29470 were found to be on chromosome #4.

EXAMPLE 2

Analysis of the Distribution of AtsPLA$_2$-δ in *Arabidopsis* Tissues

In order to confirm that the ORF (Open Reading Frame) of the said putative sPLA$_2$ gene was transcribed in *Arabidopsis*, RT-PCR was conducted.

Total RNA was extracted from *Arabidopsis* (*Arabidopsis thaliana* ecotype Columbia) mature flowers, cauline leaves, rosette leaves, inflorescences, and roots using a Nucleospin®RNA Plant kit (MACHEREY-NAGEL, Germany) in order to synthesize the standard cDNA for RT-PCR.

After 4 μg of total RNA was combined with each 10 mM of dNTP, 100 M random decamer and nuclease-free distilled water (D.W.) in the tube and stirred, it was allowed to react at 65° C. for 5 minutes. Then the tube was placed on ice. After RT-PCR buffer, RNase inhibitor and 0.1 M DTT were added to the tube, it was allowed to react at 42° C. for 2 minutes.

Again it was put on ice, and then was treated with 200 units of reverse transcriptase at 42° C. for 1 hour. This product was inactivated at 70° C. for 15 minutes to be a cDNA pool of each tissue. Each cDNA pool was used as a template for each RT reaction.

The gene specific primers used for RT-PCR were synthesized from the junction sites of exons in the gene on the basis of sequences of the TAIR site. Two target gene-specific primers used for RT-PCR are shown in the Table 1.

TABLE 1

Two target gene specific primers used for RT-PCR

| | |
|---|---|
| QRT-δ-S: 5'-GGTTGGATTTTCCAAGGAATGCCCTTATTCAAC (SEQ NO: 2) | 33-mer |
| QRT-δ-A: 5'-TCAAGAAGGAGAAGGGTTCATCGGAACAG (SEQ NO: 3) | 29-mer |

The internal standard 18S rRNA primers/competimers (2/8, v/v or 3/7, v/v) obtained from the QuantumRNA™ Universal 18S Internal Standards kit (Ambion) were used for quantitative RT-PCR. The PCR conditions used were 35 cycles of denaturing for 1 min at 95° C., annealing for 30 s, and polymerizing for 1 min at 73° C., followed by 10 min of elongation at 73° C. The annealing temperature of this reaction was decreased by 2° C. every fifth cycle from 64° C. to a 'touchdown' at 58° C., which provided to a total of 20 cycles.

The 253-bp fragment corresponding to AtsPLA$_2$-δ with a 315-bp fragment corresponding to 18 s rRNA, were amplified simultaneously in the same reaction. AtsPLA$_2$-δ transcripts were detected only in flower organs, confirming that AtsPLA$_2$-δ may have specific roles in particular organs such as flowers (FIG. 1).

EXAMPLE 3

Molecular Cloning of AtsPLA$_2$-δ from *Arabidopsis*

Using two gene specific primers, QRT-δ-S and QRT-δ-A (Table 1), a partial cDNA encoding, At4g29470 (AtsPLA$_2$-δ) was amplified from the total RNA of mature *Arabidopsis* flowers by RT-PCR using Superscrip™ II reverse transcriptase (Invitrogen) and Pyrobest® DNA polymerase (TaKaRa). Full-length cDNA corresponding to At4g29470 (AtsPLA$_2$-δ) was amplified from the RACE (Rapid Amplification of cDNA Ends) cDNA pool of mature *Arabidopsis* flowers constructed by using a Marathon™ cDNA Amplification Kit (Clontech). The 5'-ends of the transcripts were identified using a modified cRACE as a primer extension method (Maruyama et al., 1995). The ORFs of AtsPLA$_2$-δ were subcloned into EcoRV-cut pCR2.1-TOPO (Invitrogen) and transferred into XL1-Blue strain (Stratagene).

The cloned full-length cDNA sequence of At4g29470 was registered at the GenBank with accession number AY148347 and named as *Arabidopsis* secretory PLA$_2$-delta (AtsPLA$_2$-δ).

EXAMPLE 4

Identification of a Promoter Sequence Specially Expressing the Pollen-Specific Gene (TAIR at4g29470)

As a result of the RT-PCR, it was deducted that the promoter of the said gene may regulate the expression of the gene only in the flower. The 550 base pair site between the 3'UTR (untranslated region) of former gene (at4g29480) in front of the gene (at4g29470) and the start site of transcription (ATG) in the gene (at4g29470) was presumed to be the promoter region.

First, the genomic DNA (gDNA) of *Arabidopsis* was extracted. And then primers comprising the HindIII (5'terminal) and BamHI (3'terminal) site at the ends represented by SEQ NO: 4 and SEQ NO: 5 were synthesized (Table 2).

Using the gDNA as template, the promoter of AtsPLA$_2$-δ was amplified by touch-down PCR method using DNA polymerase (pyrobest, TAKARA) that can proofread the synthesized primers.

TABLE 2

Primers for PCR of pollen-specific promoter

A2-δ-P5-Hst:                                              35-mer
5'-GAGT<u>AAGCTT</u>AACTTGAAGATTGTGTAATCCCCTC-3'
(SEQ ID NO: 4)

A2-δ-P3-Bam:                                              35-mer
5'-CACC<u>GGATCC</u>CATGTTTCTATCTTACCTTCTCCAG-3'
(SEQ ID NO: 5)

The obtained PCR products were cleaved with each restriction enzyme and were cloned into pBl101 vectors (Clontech). As result of sequencing the said clones, it was found that each clone had a sequence identical to the promoter (FIG. 2).

Compared using an online database of plant cis-acting regulatory DNA elements, such as PLACE and PlantCARE, it was found that the sequence of the promoter has an element that induces the pollen-specific expression at many sites (FIG. 2).

EXAMPLE 5

Identification of the Spatial and Temporal Expression Patterns of AtsPLA$_2$-δ

Figure 3:
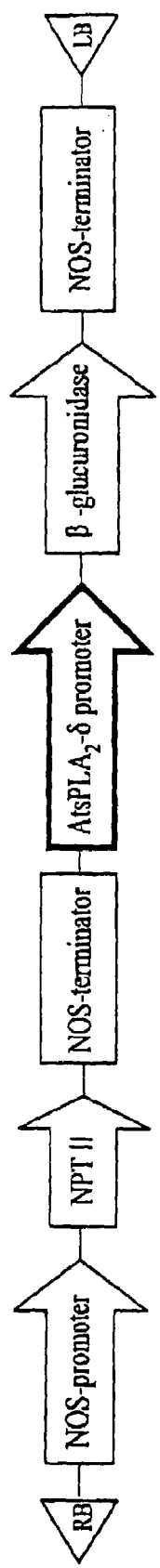
FIG. 3 shows the gene expression cassette of the pBl101 vector for cloning the pollen-specific promoter according to the present invention.

The pBl101 vector used in cloning target promoters is a binary vector for transformation with GUS (β-glucuronidase) reporter gene between left border and right border (FIG. 3). FIG. 4 shows the nucleotide sequence (SEQ NO: 6) that indicates the gene expression cassette containing AtsPLA$_2$-δ-promoter, GUS and Nos-terminator.

The promoter::GUS binary vectors were transferred to *Agrobacterium tumefaciens* GV3101 by the freeze thaw method. *Arabidopsis* plants were transformed by the in planta method (flower dipping method) using *Agrobacterium tumefaciens* GV3101.

Twenty-six independent T3 transgenic lines were generated and screened with AtsPLA$_2$-δ promoter construct, on 1× Murashige and Skoog salts (Sigma) containing 0.8% (w/v) agar medium supplemented with 50 mg/L kanamycin.

Since GUS digests a particular substrate (X-GlcA) and have a green color, the plants having the inserted GUS gene and soaked in the X-GlcA solution show the green color only in the tissue expressing the GUS gene.

For GUS histochemical staining, organs were incubated overnight with X-Gluc solution [1 mM 5-bromo-4-chloro-3-indolyl-b-glucuronide, 10 mM Na$_2$EDTA, 0.5 mM K$_3$Fe (CN)$_6$, 0.5 mM K$_4$Fe(CN)$_6$, 0.1% Triton X-100, 100 mM potassium Phosphate buffer, pH 7.0] at 37° C. After staining, the chlorophyll-containing tissues were cleared in a series of ethanol (50%, 70%, 80%, 90%, and 100%) for 20–30 min each, and then observed on a SZ4045TRPT microscope (OLYMPUS).

AtsPLA$_2$-δ was expressed only in the anther sacs and pollens (FIG. 5), although the spotted GUS activity, possibly stress-inducible, was occasionally detected in the leaves and roots of some transgenic lines containing AtsPLA$_2$-δ promoter::GUS cassette in the different sites of their chromosomes (data not shown).

Figure 5:
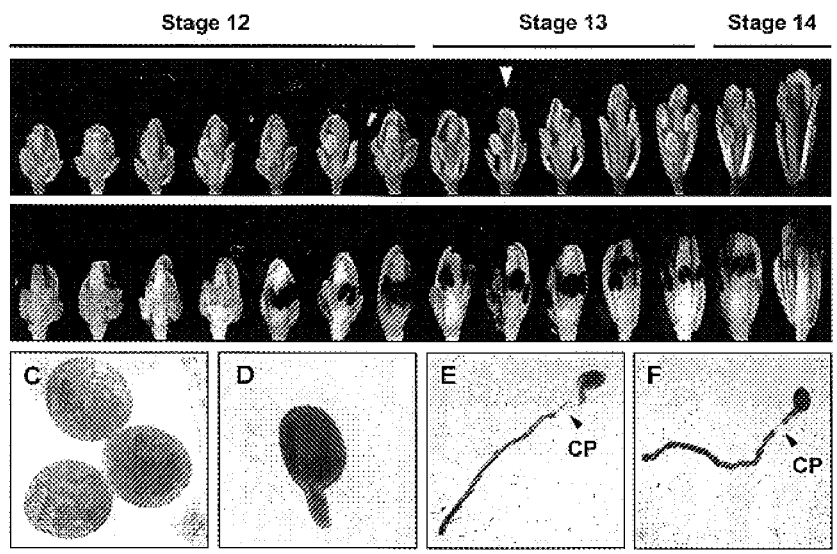
FIG. 5A–5F shows the pollen specific expression of the reporter gene 'GUS' by the pollen-specific promoter according to the present invention.

As the flower buds developed, the expression of AtsPLA$_2$-δ gradually increased corresponding to the maturation of anther sacs and pollen grains (FIG. 5). The initiation stage of the gene expression of AtsPLA$_2$-δ seems to be slightly different from the stage of yellowing of the anther.

The GUS activity decreased in the dehisced anther sacs, which probably resulted from the programmed cell death of the tapetal cells and stomium cells. On the other hand, the expression of AtsPLA$_2$-δ was continuously detected in the released pollen grains (FIG. 5A to 5D). Moreover, the GUS activity extended to the germinated pollen tubes in vitro (FIG. 5E to 5F).

Results of these experiments suggest that AtsPLA$_2$-δ have specific roles in pollen development and pollen tube growth.

What is claimed is:

1. An isolated solely pollen-specific promoter derived from *Arabidopsis* comprising a complete nucleotide sequence of SEQ ID NO: 1 derived from the *Arabidopsis* AtsPLA$_2$-δ gene and having a size of about 550 base pair.

2. A recombinant vector comprising
   an isolated solely pollen-specific promoter derived from *Arabidopsis* comprising a complete nucleotide sequence of SEQ ID NO: 1 derived from the *Arabidopsis* AtsPLA$_2$-δ gene and having a size of about 550 base pair; and
   a foreign gene fused with the said promoter and regulated by the promoter.

3. The recombinant vector according to claim 2, wherein the foreign gene is a gene degrading male fertility.

4. A plant cell transformed by the recombinant vector according to claim 2.

5. A plant cell transformed by the recombinant vector according to claim 3.

6. The isolated pollen-specific promoter of claim 1, wherein the promoter is amplified by a primer comprising a complete nucleotide sequence of SEQ ID NO: 4 and SEQ ID NO: 5.

* * * * *